United States Patent
Albrecht et al.

(10) Patent No.: US 10,991,458 B2
(45) Date of Patent: Apr. 27, 2021

(54) SYSTEM AND METHOD FOR DETECTING ACTIVATION OF A MEDICAL DELIVERY DEVICE

(71) Applicants: AMGEN INC., Thousand Oaks, CA (US); CONNECTMESMART GMBH, Lengdorf (DE)

(72) Inventors: Sabine Albrecht, Woodland Hills, CA (US); Markus Bauss, Lengdorf (DE)

(73) Assignee: AMGEN INC., Thousand Oaks, CA (US)

( * ) Notice: Subject to any disclaimer, the term of this patent is extended or adjusted under 35 U.S.C. 154(b) by 943 days.

(21) Appl. No.: 15/322,551

(22) PCT Filed: Jul. 21, 2015

(86) PCT No.: PCT/US2015/041237
§ 371 (c)(1),
(2) Date: Dec. 28, 2016

(87) PCT Pub. No.: WO2016/014457
PCT Pub. Date: Jan. 28, 2016

(65) Prior Publication Data
US 2017/0147787 A1  May 25, 2017

Related U.S. Application Data

(60) Provisional application No. 62/027,750, filed on Jul. 22, 2014.

(51) Int. Cl.
*G16H 20/10* (2018.01)
*G16H 20/17* (2018.01)
(Continued)

(52) U.S. Cl.
CPC ......... *G16H 20/10* (2018.01); *G06F 16/2455* (2019.01); *G06F 16/583* (2019.01);
(Continued)

(58) Field of Classification Search
CPC .................................................. G16H 20/10
See application file for complete search history.

(56) References Cited

U.S. PATENT DOCUMENTS

| | | | |
|---|---|---|---|
| 9,788,906 B2 * | 10/2017 | Piron | A61B 6/5247 |
| 2003/0105389 A1 * | 6/2003 | Noonan | G16H 40/67 |
| | | | 600/300 |

(Continued)

FOREIGN PATENT DOCUMENTS

| | | |
|---|---|---|
| CN | 1525832 A | 9/2004 |
| CN | 102300544 A | 12/2011 |

(Continued)

OTHER PUBLICATIONS

Extended European Search Report for European Application No. 15824123.2, dated Jan. 30, 2018.

(Continued)

*Primary Examiner* — Michael Tomaszewski
*Assistant Examiner* — Jay M. Patel
(74) *Attorney, Agent, or Firm* — Marshall, Gerstein & Borun LLP

(57) ABSTRACT

Methods and systems for determining that a medical delivery device has been activated may be provided. According to certain aspects, a user captures a first image to determine if a medical delivery device is ready to be activated. The first image is transmitted to a health care provider which verifies that the medical delivery device should be activated. If the medical delivery device is to be activated, an electronic device instructs the user to activate the medical delivery device. Subsequently, the user transmits details about the activation of the medical delivery device to the health care provider to update a medical record.

24 Claims, 6 Drawing Sheets

(51) Int. Cl.
*G16H 10/60* (2018.01)
*G06F 16/583* (2019.01)
*G06F 16/2455* (2019.01)
*G16H 40/67* (2018.01)
*G16H 30/20* (2018.01)
*A61M 5/20* (2006.01)

(52) U.S. Cl.
CPC ............ *G16H 10/60* (2018.01); *G16H 20/17* (2018.01); *G16H 30/20* (2018.01); *G16H 40/67* (2018.01); *A61J 2200/30* (2013.01); *A61M 5/20* (2013.01)

(56) References Cited

U.S. PATENT DOCUMENTS

| | | | | |
|---|---|---|---|---|
| 2006/0047538 | A1* | 3/2006 | Condurso | G06F 19/3456 705/3 |
| 2006/0206356 | A1* | 9/2006 | Vanderveen | G06F 19/3468 705/2 |
| 2007/0260491 | A1* | 11/2007 | Palmer | G06F 19/3418 705/3 |
| 2007/0299687 | A1* | 12/2007 | Palmer | G06Q 50/22 705/2 |
| 2008/0111883 | A1 | 5/2008 | Maolin et al. | |
| 2008/0195249 | A1* | 8/2008 | Rousso | A61B 5/417 700/231 |
| 2010/0100234 | A1* | 4/2010 | Osborne | A61J 1/2096 700/228 |
| 2010/0161113 | A1* | 6/2010 | Tribble | B65B 7/2821 700/225 |
| 2011/0153360 | A1* | 6/2011 | Hanina | G16H 10/20 705/3 |
| 2011/0295416 | A1 | 12/2011 | Aquilonius et al. | |
| 2011/0313350 | A1 | 12/2011 | Krulevitch et al. | |
| 2012/0140068 | A1 | 6/2012 | Monroe et al. | |
| 2012/0265271 | A1* | 10/2012 | Goetz | A61N 1/36128 607/59 |
| 2013/0138452 | A1* | 5/2013 | Cork | G06Q 50/22 705/2 |
| 2013/0165906 | A1 | 6/2013 | Kitaoka et al. | |
| 2013/0172730 | A1* | 7/2013 | Cohen | A61B 6/12 600/424 |
| 2013/0173284 | A1* | 7/2013 | Hyde | G16H 50/30 705/2 |
| 2013/0197927 | A1* | 8/2013 | Vanderveen | G06Q 50/24 705/2 |
| 2013/0204227 | A1* | 8/2013 | Bochenko | A61M 5/31 604/506 |
| 2013/0204433 | A1* | 8/2013 | Gupta | G06Q 50/22 700/239 |
| 2013/0268291 | A1* | 10/2013 | Lynn | G16H 50/20 705/2 |
| 2014/0039672 | A1* | 2/2014 | Niinisto | A61J 7/0427 700/240 |
| 2014/0055267 | A1* | 2/2014 | Rothschild | A61J 7/0084 340/573.1 |
| 2014/0058292 | A1* | 2/2014 | Alford | A61B 8/0816 601/2 |
| 2014/0081234 | A1 | 3/2014 | Eggert et al. | |
| 2014/0100442 | A1* | 4/2014 | Begin | A61B 8/12 600/411 |
| 2014/0132413 | A1* | 5/2014 | Fox | G16H 40/20 340/573.1 |
| 2014/0180707 | A1* | 6/2014 | Kukreja | G16H 20/10 705/2 |
| 2015/0057622 | A1* | 2/2015 | Hyde | G06F 16/2455 604/290 |
| 2015/0058368 | A1* | 2/2015 | Hyde | G06F 19/00 707/756 |
| 2015/0119652 | A1* | 4/2015 | Hyde | A61B 5/7445 600/301 |
| 2016/0030679 | A1* | 2/2016 | Nielsen | G06F 19/3456 604/189 |
| 2017/0316157 | A1* | 11/2017 | Riedel | G06K 9/3258 |

FOREIGN PATENT DOCUMENTS

| | | | |
|---|---|---|---|
| CN | 103108664 A | 5/2013 | |
| CN | 103520806 A | 1/2014 | |
| CN | 103687636 A | 3/2014 | |
| WO | WO-2011/062934 A1 | 5/2011 | |
| WO | WO-2011062934 * | 5/2013 | ............ G06F 19/34 |
| WO | WO-2013096718 A2 | 6/2013 | |

OTHER PUBLICATIONS

Chinese Patent Application No. 201580040177.7, First Office Action, dated Nov. 14, 2018.
International Search Report and Written Opinion, International Application No. PCT/US15/41237, dated Oct. 26, 2015.
Chinese Patent Application No. 201580040177, Third Office Action, dated Feb. 26, 2020.
Australian Patent Application No. 2015292918, Examination Report No. 1, dated Mar. 23, 2020.
Australian Patent Application No. 2015292918, Examination Report No. 2, dated Jul. 23, 2020.
Australian Patent Application No. 2015292918, Examination Report No. 3, dated Dec. 15, 2020.
Australian Patent Application No. 2015292918, Examination Report No. 4, dated Mar. 17, 2021.

\* cited by examiner

SYSTEM AND METHOD FOR DETECTING ACTIVATION OF A MEDICAL DELIVERY DEVICE

TECHNICAL FIELD

This application is generally related to verifying that a drug delivery device has been activated, and, more specifically, to systems and methods for verifying that a medical delivery device has been activated.

BACKGROUND

A medication regimen often requires that a patient is administered a medication on a regular schedule. Many medication regimens allow for a patient to administer the medication himself or herself without requiring a visit to a health care provider (HCP). Some patients may either forget or become temporarily unable to self-administer a medication according to the regimen, potentially resulting significant health consequences. Other health consequences may result from the operation of a wrong delivery device usable for delivering the medication. Adverse consequences for the patient may be avoided if an HCP or the patient is alerted that a scheduled injection was missed. Improving medication compliance can assist in improving health care outcomes.

Thus, a need exists for a system, an electronic device and a method that enable an HCP or a patient to verify that the delivery device has been properly operated (for example, activated).

SUMMARY OF THE DISCLOSURE

In a first embodiment, a system for determining that a medical delivery device has been activated is provided. The system comprises at least an electronic device, and the electronic device comprises (i) an image sensor configured to capture images; and (ii) a user interface configured to display content. The system further comprises one or more processors adapted to interface with the image sensor and the user interface, wherein the one or more processors are configured to (1) receive a first set of image data from the image sensor, (2) analyze the first set of image data to determine that a medical delivery device is ready to deliver a medication to a patient, (3) receive a second set of image data from the image sensor, (4) analyze the second set of image data to determine that the medical delivery device has been activated, and (5) cause the user interface to indicate that the medical delivery device has been activated.

The system may include at least one further component for transmitting digital data to the electronic device and from the electronic device to the at least one further component. The at least one further component may be for example at least one of an electronic network (such as the internet) and a server (e.g. a cloud server) which are operatively connected to the electronic device. At least one (including, in one example, all) of the processors may be part of the server. Alternatively, all of the at least one processors may be part of the electronic device (in that case, the system may consist of the electronic device).

In another, second embodiment, a method for enabling a user to detect the activation of a medical delivery device with an application executing on a web-enabled mobile device is provided. The web-enabled mobile device includes one or more processors, a memory coupled to the one or more processors, and an image sensor configured to capture images of the medical delivery device, and the method comprises (1) the application causing the image sensor to capture a first image of the medical delivery device; (2) analyzing, by the one or more processors, the first image to determine that the medical delivery device is ready to deliver a medication to a patient; (3) the application causing the image sensor to capture a second image of the medical delivery device; (4) analyzing, by the one or more processors, the second image to determine that the medical delivery device was activated; and (5) indicating, via the user interface in the application, that the medical delivery device was activated.

In another, third embodiment, a computer-implemented method for enabling a user to detect a medical delivery device activation is provided. The method includes capturing, by an image sensor, a first image of the medical delivery device, and analyzing, by one or more processors, the first image to determine that the medical delivery device is ready to deliver a medication to a patient. Subsequently, the method includes capturing, by the image sensor, a second image of the medical delivery device, and analyzing, by the one or more processors, the second image to determine if the medical delivery device was activated. Additionally, the method includes indicating, via the user interface, that the medical delivery device was activated.

In still another, fourth embodiment, a non-transitory, computer-readable storage medium having computer-executable instructions stored in a memory is provided. The instructions, when executed on one or more processors in a web-enabled mobile device provide an application to operate to allow a user to detect that a medical delivery device has been activated. The computer executable instructions comprise instructions for the application to cause an image sensor to capture a first set of image data depicting the medical delivery device and analyze, by the one or more processors, the first set of image data to determine that the medical delivery device is ready to deliver a medication to a patient. The instructions further cause the application to cause the image sensor to capture a second set of image data depicting the medical delivery device. The instructions still further cause the application to analyze, by the one or more processors, the second set of image data to determine that the medical delivery device was activated and indicate, via the user interface in the application, that the medical delivery device was activated.

In the following, example embodiments A to Z and AA are described in general words. These embodiments are non-limiting examples of the invention. Features of different embodiments disclosed herein can be combined wherever technically expedient and feasible. Specifically, a feature of one embodiment which has the same or a similar function to another feature of another embodiment can be exchanged with said other feature, and a feature of one embodiment which adds an additional function to another embodiment can for example be added to said other embodiment.

A. A system for determining that a medical delivery device has been activated, the system comprising at least an electronic device, the electronic device comprising (i) an image sensor configured to capture images; (ii) a user interface configured to display content; and (iii) one or more processors adapted to interface with the image sensor and the user interface, wherein the one or more processors are configured to (1) receive a first set of image data from the image sensor, (2) analyze the first set of image data to determine whether a medical delivery device is ready to deliver a medication to a patient, (3) if the result of analyzing the first set of image data is that the medical delivery device is ready to deliver the medication to the patient, (4) receive a second set of image data from the image sensor, (5) analyze the second set of image data to determine whether the second image indicates that the medical delivery device has been activated, and (6) if the result of analyzing the second set of image data is that the medical device has been activated, and (7) cause the user interface to indicate that the medical delivery device has been activated.

The system may include at least one further component for transmitting digital data to the electronic device and from the electronic device to the at least one further component. The at least one further component may be for example at least one of an electronic network (such as the internet) and a server (e.g. a cloud server) which are operatively connected to the electronic device. At least one (including, in one example, all) of the processors may be part of the server. Alternatively, all of the at least one processors may be part of the electronic device (in that case, the system may consist of the electronic device).

Generally, it may be determined whether the medical delivery device has been activated by analyzing the second set of image data whether the second set of image data indicates that the medical delivery device has been activated. For example, this involves determining whether the second set of image data represents at least at least one characteristic (e.g. image feature) indicative that the medical delivery device has been activated. In one example, this can be done by comparing the second set of image data to another set of image data (which may be received by the processor), and determining, based upon the result of that comparison, whether the second set of image data indicates that the medical delivery device has been activated. The other set of image data may be predetermined (e.g. generated before execution of the disclosed method ensues and stored in a database) and retrieved to serve as input for the comparison. Alternatively, the other set of image data may be generated by the processor. For example, the other set of image data may be contained in the first set of image data. The at least one characteristic indicative that the medical delivery device has been activated may be determined by comparing the second set of image data to a predetermined set of image data (such as the other set of image data) representing the at least one characteristic indicative that the medical delivery device has been activated. Alternatively or additionally, the at least one characteristic indicative that the medical delivery device has been activated may be determined by comparing the second set of image data to the first set of image data and detecting a difference between the respective representations of the medical delivery device, which difference corresponds to the at least one characteristic indicative that the medical delivery device has been activated. Wherever in this disclosure a comparison of image data or images (for example digital images) is mentioned, such comparison may be effected by for example a pixel-wise comparison or a block-wise similarity analysis between color values of the respective sets of image data or images (for example digital images). Any other suitable algorithm may also be applied to the same effect. In another example, determining whether the second set of image data represents at least the at least one characteristic indicative that the medical delivery device has been activated may be done by analyzing whether the second set of image data contains or lacks a certain image feature (such as a two-dimensional graphical code, e.g. a barcode, a QR code, or a GS1 code), the presence or absence of that image feature being the at least one characteristic indicative that the medical delivery device has been activated. In an even further example, determining whether the second set of image data image represents at least the at least one characteristic indicative that the medical delivery device has been activated may be done by analyzing only the second set of image data, for example as to its color distribution (color histogram). The color distribution being within a predetermined limit equal to a predetermined color histogram can be set as a condition for the second image indicating that the medical delivery device has been activated. If such an equality is determined, it is thus determined that the medical delivery device has been activated.

B. The system according to the first embodiment or embodiment A, wherein the first set of image data contains image data representative of at least one of a 2-D barcode or a readiness characteristic, wherein the readiness characteristic comprises at least one of a needle cap and a protruded button.

C. The system according to embodiment B, wherein to determine that the medical delivery device is ready to deliver a medication to a patient, the one or more processors are configured to verify that the first set of image data contains image data representative of the readiness characteristic.

D. The system according to the first embodiment or embodiment A, wherein the second set of image data contains image data representative of at least one of a needle shield, an indication that the medication has been expelled, or a depressed button.

E. The system according to the first embodiment or embodiment A, further comprising a memory to store a medication regimen (for example, information representing a medication regimen) of the patient, wherein the medication regimen contains a schedule of when a user is to administer the medication to the patient.

F. The system according to embodiment E, wherein the one or more processors are further configured to (1) cause the user interface to display, based on evaluating the stored medication regimen, a reminder of when the medication regimen indicates that the user is to administer the medication, and (2) after confirming, for example based on the result of analyzing the second set of image data, that the medical delivery device has administered the medication, cause the user interface to display when a next medication in the medication regimen is to be administered.

G. The system according to embodiment E, wherein the one or more processors are further configured to transmit, via a communication network, an alert to a health care provider associated with the patient when it is determined, for example based on the result of analyzing the second set of image data, that no medication has been delivered as scheduled in the medication regimen.

H. The system according to embodiment B, wherein the one or more processors are further configured to (1) transmit, to a remote server via a communication network, the first set of image data; and (2) receive, from the remote server via the communication network, a notification to activate the medical delivery device for example if the result of analyzing the first set of image data is that the medical delivery device is ready to deliver the medication to the patient.

I. The system according to embodiment H, wherein transmitting the first set of image data causes the remote server to (1) receive, via the communication network, the first set of image data from the electronic device; (2) obtain, from the first set of image data, an identifier associated with the medical delivery device; (3) compare the identifier to a record contained in an authentication database; (4) determine that the medication should be delivered to the patient; and (5) transmit, to the electronic device, a notification to activate the medical delivery device.

J. The system according to embodiment H, wherein receiving the notification to activate the medical delivery comprises receiving, via the communication network, a notification that the remote server determined the medication is not counterfeit, the medication is not expired, and the medication has not been recalled.

K. The system according to embodiment B, wherein the one or more processors are further configured to transmit, to the remote server via the communication network, an indication that the medical delivery device was activated.

L. The system according to embodiment K, wherein transmitting the indication that the medical delivery device was activated causes the remote server to update a medical record in a patient record database with information about a delivery event, wherein the information comprises at least one of a time and date of the delivery, a location of the delivery event, a name of the medication, a batch number, a lot number, or a name of the user who administered the medication.

M. A method for enabling a user to detect the activation of a medical delivery device with an application executing on a web-enabled mobile device, where the web-enabled mobile device includes one or more processors, a memory coupled to the one or more processors, and an image sensor configured to capture images of the medical delivery device, the method comprising (1) the application causing the image sensor to capture a first image of the medical delivery device; (2) analyzing, by the one or more processors, the first image to determine whether the medical delivery device is ready to deliver a medication to a patient; (3) the application causing, if the result of analyzing the first image data is that the medical delivery device is ready to deliver the medication to the patient, the image sensor to capture a second image of the medical delivery device; (4) analyzing, by the one or more processors, the second image to determine whether the medical delivery device has been activated; and (5) if the result of analyzing the second image is that the medical delivery device has been activated, indicating, via the user interface in the application, that the medical delivery device was activated.

Generally, it may be determined whether the medical delivery device has been activated by analyzing the second image whether the second image indicates that the medical delivery device has been activated. For example, this involves determining whether the second image represents at least one characteristic indicative that the medical delivery device has been activated. In one example, this can be done by comparing the second image to another image (which is received as part of the disclosed method), and determining, based upon the result of that comparison, whether the second image indicates that the medical delivery device has been activated The other image may be predetermined (e.g. generated before execution of the disclosed method ensues and stored in a database) and retrieved to serve as input for the comparison. Alternatively, the other image may be generated during execution of the disclosed method (for example, as part of the disclosed method). For example, the other image may be contained in the first image. The at least one characteristic indicative that the medical delivery device has been activated may be determined by comparing the second image to a predetermined image (such as the other image) representing the at least one characteristic indicative that the medical delivery device has been activated. Alternatively or additionally, the at least one characteristic indicative that the medical delivery device has been activated may be determined by comparing the second image to the first image and detecting a difference between the respective representations of the medical delivery device, which difference corresponds to the at least one characteristic indicative that the medical delivery device has been activated. Wherever in this disclosure a comparison of image data or images (for example digital images) is mentioned, such comparison may be effected by for example a pixel-wise comparison or a block-wise similarity analysis between color values of the respective sets of image data or images (for example digital images). Any other suitable algorithm may also be applied to the same effect. In another example, determining whether the second image represents at least the at least one characteristic indicative that the medical delivery device has been activated may be done by analyzing whether the second image contains or lacks a certain image feature (such as a two-dimensional graphical code, e.g. a barcode, a QR code, or a GS1 code), the presence or absence of that image feature being the at least one characteristic indicative that the medical delivery device has been activated. In an even further example, determining whether the second image represents at least the at least one characteristic indicative that the medical delivery device has been activated may be done by analyzing only the second image, for example as to its color distribution (color histogram). The color distribution being within a predetermined limit equal to a predetermined color histogram can be set as a condition for the second image indicating that the medical delivery device has been activated. If such an equality is determined, it is thus determined that the medical delivery device has been activated.

N. The method according to the second or third embodiment or embodiment M, wherein analyzing the first image comprises identifying, from the first image, at least one of a QR code and a readiness characteristic, wherein the readiness characteristic comprises at least one of a needle cap or a protruded button.

O. The method according to the second or third embodiment or embodiment M, wherein analyzing the second image comprises identifying, from the second image and for example as the at least one characteristic indicative that the medical delivery device has been activated, at least one of a needle shield, an indication that the medication has been expelled (i.e. discharged), or a depressed button.

P. The method according to the second or third embodiment or embodiment M, further comprising (1) receiving information representing a medication regimen of the patient, wherein the medication regimen contains a schedule of when a user is to administer the medication to the patient; (2) displaying, via the user interface in the application, an indication of when a medication regimen indicates that the user is to deliver the medication; and (3) after determining that the medical delivery device has delivered the medication, displaying, via the user interface in the application, when a next medication in the medication regimen is to be delivered.

Q. The method of embodiment P, further comprising the application alerting, via a communications network, a health care provider associated with the patient when no it has been determined, for example based on the result of analyzing the second image, that medication has been delivered as scheduled in the medication regimen.

R. The method according to the second or third embodiment or embodiment M, further comprising (1) transmitting from the web-based mobile device, to a remote server via a communication network, the first image; and (2) if the result of analyzing the first image is that the medical delivery device is ready to deliver the medication to the patient, receiving at the web-based mobile device, via the communication network, a notification to activate the medical delivery device.

S. The method of embodiment R, wherein transmitting the first image causes the remote server to (1) receive, via the communication network, the first image from the web-enabled mobile device; (2) read, from the first image by one or more processors at the remote server, an identifier associated with the medical delivery device; (3) compare, by the one or more processors at the remote server, the identifier to a record contained in an authentication database to determine that the medication should be delivered to the patient; and (4) transmit, via the communication network, a notification to activate the medical delivery device to the web-enabled mobile device.

T. The method of embodiment S, wherein transmitting the first image further causes the remote server to analyze the authentication database to determine that the medication is not counterfeit, the medication is not expired, and the medication has not been recalled.

U. A computer-implemented method for determining that a medical delivery device has been activated, the method comprising (1) receiving, via a communication network, a first image, wherein the first image depicts the medical delivery device; (2) analyzing, by one or more processors, the first image to obtain an identification of the medical delivery device; (3) using the identification, determining, by the one or more processors, whether medication within the medical delivery device should be administered to a patient for example based on comparing the identification to pre-determined information defining the medication to be delivered; (4) if it has been determined that the medication within the delivery device should be administered to the patient, transmitting, via the communication network, a first indication that a user should administer the medication or should activate the delivery device; (5) receiving, via the communication network, a second indication that the medical delivery device has been activated; and (6) based on the second indication, updating, by the one or more processors, a medical record corresponding to the patient.

V. The computer-implemented method according to the fourth embodiment or embodiment U, wherein analyzing the first image further comprises (1) analyzing, by the one or more processors, the first image to detect a barcode depicted in the first image; (2) determining, by the one or more processors, a Universal Resource Locator (URL) indicated by the barcode; and (3) obtaining, by the one or more processors, the identification from information hosted at the indicated URL.

W. The computer-implemented method according to the fourth embodiment or embodiment U, wherein analyzing the first image further comprises analyzing, by the one or more processors, extracted data corresponding to the first image, wherein the extracted data was extracted via a Near-Field Communication (NFC) sensor.

X. The computer-implemented method according to the fourth embodiment or embodiment U, wherein determining whether the medication should be administered further comprises (1) using the identifier, querying, by the one or more processors, an authentication database that stores information relating to the medication; and (2) determining, by the one or more processors, that the authentication database indicates that the medication is not counterfeit, expired, or recalled.

Y. The computer-implemented method according to the fourth embodiment or embodiment U, wherein receiving the second indication further comprises (1) receiving, via the communication network, a second image, wherein the second image depicts the medical delivery device; and (2) analyzing, by the one or more processors, the second image to determine that the medical delivery device has been activated.

Z. A non-transitory computer-readable storage medium having a memory and computer-executable instructions (e.g. embodied in a computer program) stored in the memory, which instructions, when executed on at least one processor of at least one computer, cause the at least one computer to execute the computer-implemented method of any one of the fourth embodiment or embodiments U to Y, the method according to any one of the second embodiment or embodiments A to T, or the computer-implemented method according to the third embodiment. The computer program (which can be stored on the non-transitory computer-readable storage medium, specifically in its memory) also forms part of the invention.

AA. At least one computer having at least one processor, the at least one computer being operatively coupled to the non-transitory computer-readable storage medium of any one of the fifth embodiment or embodiment Z, for executing, by the at least one processor, the instructions stored in the memory of the non-transitory computer-readable storage medium.

As used in this disclosure, the terminology "determining that [something occurs]" also means "determining whether [something has occurred], and if it is determined that [the something has occurred, continuing with the following method step]".

As used in this disclosure, detecting the activation of the medical delivery device is used as a proxy for detecting that a medication has been administered to a patient. To this end, the claimed methods and systems do not purport to require a surgical or therapeutic step (i.e., an invasive step) involving the actual administration of the medication to the patient. Instead, the disclosed methods and systems relate to digital data processing. Accordingly, envisioned embodiments may involve dispensing the medication into the atmosphere and/or delivering the medication into an artificial (e.g. non-human and non-animal) dummy body during a testing procedure. Accordingly, as used in this disclosure, the phrase "activating the medical delivery device" refers operating the medical delivery device, i.e. putting to function, in its broadest sense.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

DETAILED DESCRIPTION

Overview

Figure 1:
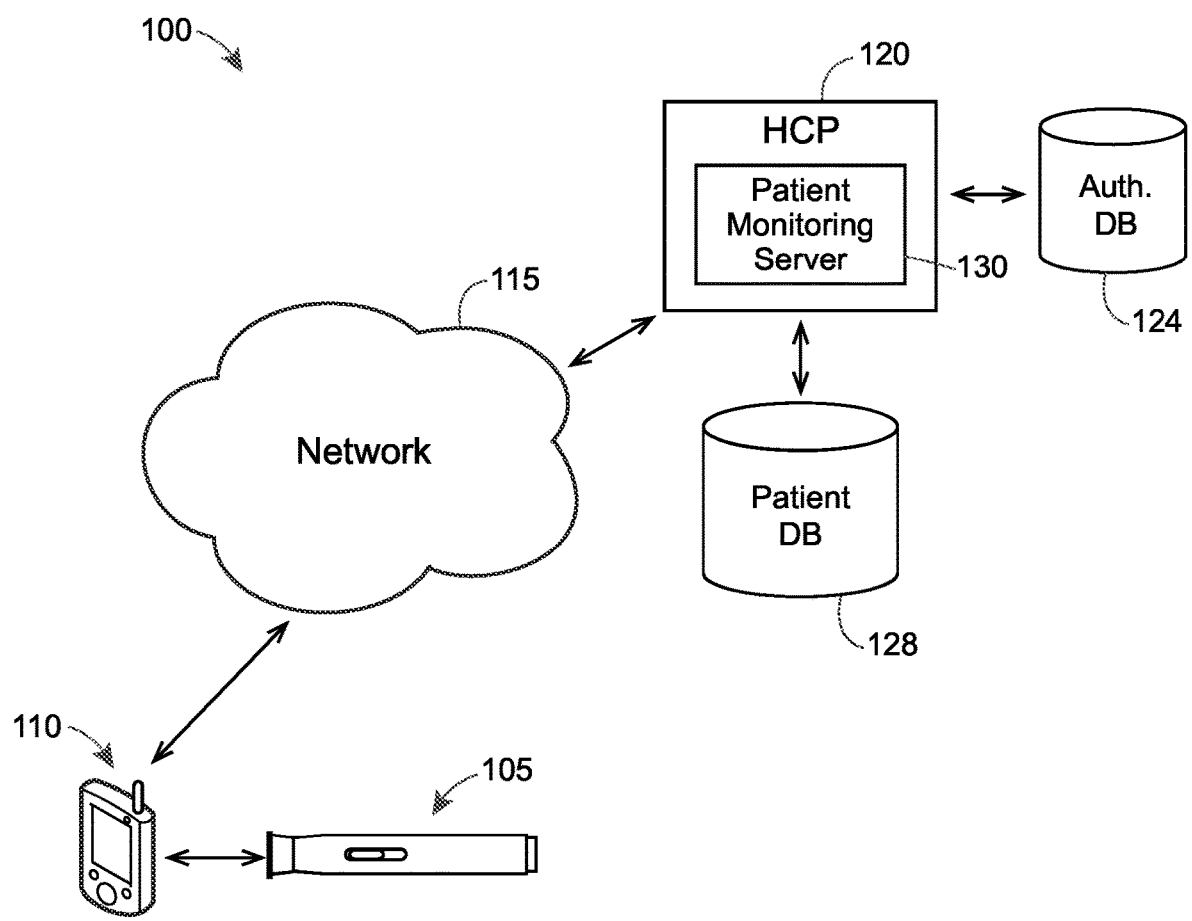
FIG. 1 depicts an example environment including components and entities associated with verifying that a medical delivery device has been activated.

The novel systems and methods disclosed herein relate generally to detecting that a medical delivery device has been activated. Detecting that the medical delivery device has been activated may indicate and/or be used as a proxy for detecting that a medication has been delivered to the patient. In particular, the systems and methods utilize at least one image sensor that is capable of capturing an image and/or utilizing augmented reality (AR) techniques to determine that the medical delivery device should be used on the patient. If it is determined that the medical delivery device should be activated, the user is given an indication to activate the medical delivery device. After activating the medical delivery device, the image sensor may again capture an image and/or utilize AR techniques to determine if the medical delivery device was activated. According to certain aspects, a health care record associated with the patient is updated to include details about the delivery event.

The systems and methods therefore offer a benefit to patients by enabling a health care provider (HCP) to remotely monitor a patient to determine if the patient is complying with a prescribed medication regimen. By monitoring its patients' compliance with their respective medication regimens, the HCP can determine which patients may need extra oversight to ensure that a scheduled medication delivery is not missed. Improving patient compliance with medication regimens can improve medical outcomes in patients, resulting in fewer costs to the HCP in the course of treating potentially preventable conditions. Further, by detecting the activation of the medical delivery device using AR techniques, the activation can be tracked by the systems and methods described herein without any modification of the medical delivery device itself. This lack of modification may reduce manufacturing costs causing the savings to be passed on to the patient. Additionally, the systems and methods can assist in the technological field of pharmacovigilance, the monitoring for and prevention of adverse drug events experienced by patients.

Accordingly, the present systems and methods improve a technical field, namely medical technology. Conventionally, when a medical delivery device is activated, for example in order to use it to administer a medication to a patient, the patient's HCP is unaware of the scheduled administration event. As a result, the HCP may not learn that a patient has missed a scheduled administration event until the patient's next visit to the HCP. In some cases, this delay may cause negative health consequences. Conversely, the present systems and methods enable the HCP to almost immediately learn of the scheduled administration event. Accordingly, if the HCP fails to receive an indication of a scheduled administration event, it can act quickly to reduce the likelihood that said negative health consequences occur.

As used herein, the term "health care provider" generally refers to a party or entity (e.g., a business or other organizational entity) that provides health care products or services to patients, e.g., by treating medical conditions or providing medications. Typically, but not necessarily, a health care provider may be a hospital, a doctor, or other similar entity or individual (e.g., an outpatient care facility or a caretaker that assists patients in complying with medication regimens).

The term "patient" refers to a person that is receiving care from an HCP or is scheduled to self-administer the drug. A "user" refers to a person operating the medical delivery device and/or operating the electronic device in accordance with the disclosed systems and methods. In some cases, the user and the patient may be the same person (i.e., the patient is scheduled to self-administer the medication), and in other cases, the user and patient may be two different people (i.e., the user is a caretaker or other individual assisting the patient in administering the medication).

Although the following text sets forth a detailed description of numerous different embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

Example Environment

FIG. 1 depicts an example environment 100 associated with verifying that a medical delivery device has been activated by a patient. Although FIG. 1 depicts certain entities, components, and devices, it should be appreciated that additional or alternative entities and components are envisioned.

As illustrated in FIG. 1, the environment 100 includes a medical delivery device 105. Although the medical delivery device depicted is an autoinjector, it should be appreciated that any medical delivery device is envisioned. For example, the medical delivery device may alternatively be an on-body injector, inhaler, a drip chamber, an eye dropper, a nasal spray, a nebulizer, or any other device capable of delivering a medication to a patient. Typically, the medical delivery device 105 is provided to the patient in accordance with a medication regimen.

According to embodiments, the environment 100 also includes an electronic device 110 containing at least one image sensor capable of capturing a first image of the medical delivery device 105 prior to the user activating the medical delivery device 105 and a second image of the medical delivery device 105 after the user activates the medical delivery device 105. The at least one image sensor may be capable of capturing image data automatically and/or in response to a user interaction. The electronic device 110 is further capable of executing applications stored in a memory therein. In some cases, the electronic device 110 is a device belonging to the patient. In other cases, the electronic device 110 is a device belonging to the user. It should be appreciated that any type of electronic device comprising at least one image sensor and capable of executing applications is envisioned. Accordingly, the electronic device 110 may be a web-enabled electronic device, e.g. a smartphone, tablet, notebook computer, web-enabled camera, dedicated medical delivery verification device, and/or the like. The image sensor may be part of a digital camera, e.g. of a digital camera built into the electronic device 100. Any images or image data mentioned herein are represented by for example digital image or digital image data in an electronic format, respectively.

In some embodiments, the first image of the medical delivery device 105 prior to activating the medical delivery device 105 depicts at least one characteristic of the medical delivery device 105 which is only present if the medical delivery device 105 has not been activated. For example, in embodiments in which the medical delivery device 105 is an autoinjector, the first image may depict a needle cap that must be removed prior to delivering the medication. Similarly, in some embodiments, the first image may also depict a button in a protruded position indicating that the medical delivery device 105 has not been activated. These characteristics may be detected through utilizing AR techniques by the electronic device 110. Further, according to some embodiments, the first image of the medical delivery device 105 may also include a tag associated with the medical delivery device 105. The tag may be a 2-D barcode (such as a QR code, a GS1 code, or another similar code), a 3-D barcode, an RFID tag, an NFC tag, or any other format capable of storing identification information. In some cases, the tag may be located or disposed on the medical delivery device 105; in other cases, the tag may be located or disposed on packaging associated with the medical delivery device 105. In embodiments in which the tag is located or disposed on the packaging associated with the medical delivery device 105 and the tag is in a barcode format, the "first image" may include multiple images captured by the electronic device 110. In embodiments in which the tag is an NFC tag, the electronic device 110 can extract the identification information using an NFC receiver and transmit any extracted information in digital format along with the first image.

In further embodiments, the second image of the medical delivery device 105 after activating the medical delivery device 105 depicts at least one characteristic of the medical delivery device 105 that is present if the medical delivery device 105 has been activated. The electronic device 110 may be configured to analyze the second image to determine if the medical delivery device 105 has been activated. For example, one common characteristic that may be present, in some cases, is a depiction that a chamber storing the medication is empty. As another example, if the medical delivery device 105 includes an autoinjector, the second image may depict a needle shield that is exposed after activating medical delivery device 105 (e.g. the autoinjector) and/or that a button is now in a depressed position. According to some embodiments, after the electronic device 110 utilizes AR techniques to determine that the medical delivery device 105 has been activated, the electronic device 110 may generate an indication or notification that the medical delivery device 105 has been activated.

As used in this disclosure, detecting the activation of the medical delivery device is used as a proxy for detecting that a medication has been administered to a patient. To this end, the claimed methods and systems do not purport to require a surgical or therapeutic step (i.e., an invasive step) involving the actual administration of the medication to the patient. Instead, the disclosed methods and systems relate to digital data processing. Accordingly, envisioned embodiments may involve dispensing the medication into the atmosphere and/or delivering the medication into an artificial (e.g. non-human and non-animal) dummy body during a testing procedure. Accordingly, as used in this disclosure, the phrase "activating the medical delivery device" refers operating the medical delivery device, i.e. putting to function, in its broadest sense.

According to embodiments, the electronic device 110 may be configured to transmit the first image of the medical delivery device 105 to an HCP 120 via a network 115. The electronic device 110 may be further configured to transmit, to the HCP 120 via the network 115, the indication that the medical delivery device 105 has been activated. The network 115 may facilitate any type of data communication via any standard or technology (e.g., GSM, CDMA, TDMA, WCDMA, LTE, EDGE, OFDM, GPRS, EV-DO, UWB, IEEE 802 including Ethernet, WiMAX, and/or others). According to embodiments, the HCP 120 may include one or more patient monitoring server(s) 130 configured to facilitate the functionalities discussed herein. Although FIG. 1 depicts the patient monitoring server 130 as part of the HCP 120, it should be appreciated that the patient monitoring server 130 may be separate from (and connected to or accessible by) the HCP 120. Further, in some embodiments, some or all functionalities of the patient monitoring server 130 described herein may be implemented locally on the electronic device 110.

The patient monitoring server 130 may be coupled to both an authentication database 124 configured to store authentication data associated with medications and a patient record database 128 configured to store medical records of patients, including medication regimens. The contents of both the authentication database 124 and the patient record database 128 may be maintained by one or more third party entities in combination with, or in place of, the HCP 120. For example, medication manufacturers may update the contents of the authentication database 124 with records containing information about new batches of medication or information about a recall for a particular medication. As another example, an HCP other than HCP 120 may update the patient record database 128 to reflect medication delivery events that occurred at the separate HCP.

In embodiments in which the tag is in a barcode format, after receiving the first image, the patient monitoring server 130 may extract encoded identification information from the tag associated with the medical device 105. In embodiments that utilize NFC, the identification information may already be extracted by electronic device 110 and transmitted to patient monitoring server 130 along with the first image. The identification information may include information identifying the name of the medication, expiry information for the medication, a unique serial number associated with the medication, a batch and/or lot number for the medication, a quantity of medication inside the medical delivery device 105, and/or other pertinent characteristics. The patient monitoring server 130 may analyze the extracted information to determine whether a patient should receive the medication contained inside the medical delivery device 105. According to some embodiments in which the tag is in a barcode format, if the patient monitoring server 130 is unable to read the information encoded in the tag, the patient monitoring server 130 may transmit, to the electronic device 110, a request to capture another image. In further embodiments, this request may also include an instruction on how to capture the image in a way that makes the tag associated with medical device 105 more readable by the patient monitoring server 130.

In some embodiments, the patient monitoring server 130 may additionally compare a name of the medication identified in the tag to a patient record stored in the patient record database 128 to ensure that the medication will be administered in compliance with the medication regimen. For example, a patient may be prescribed to receive two different medications on different schedules. Accordingly, the patient monitoring server 130 may detect that the user is about to administer the wrong medication. After verifying that the patient should receive the medication, the patient monitoring server 130 may send an indication to the electronic device 110 to administer the medication.

In further embodiments, the patient monitoring server 130 may receive an indication from the electronic device 110 that the medication delivery device 105 has been successfully activated. In response to receiving the indication that the medical delivery device 105 has been activated, the patient monitoring server 130 may update the patient record in the patient record database 128 to include details from the associated activation event. Such details may include, for example, the time and date of the activation, the location of the activation, the name of the medication, the name of the person who activated the medical delivery device 105, the quantity of the medication to be delivered, the batch and/or lot number of the medication, and/or the like.

In some embodiments, a payer (not depicted) for or purchaser of the medication may have access to the patient record database 128 to monitor the compliance with a medication regimen by the patient. The payer/purchaser may be an entity that is financially liable for the costs of a medication in addition to the patient (e.g., a medical insurance provider). According to embodiments, based on the patient's compliance with the medication regimen, the payer/purchaser may alter its share of the financial liability for the medication associated with the patient.

Example Method of Detecting Activation and Updating Patient Records

Figure 2:
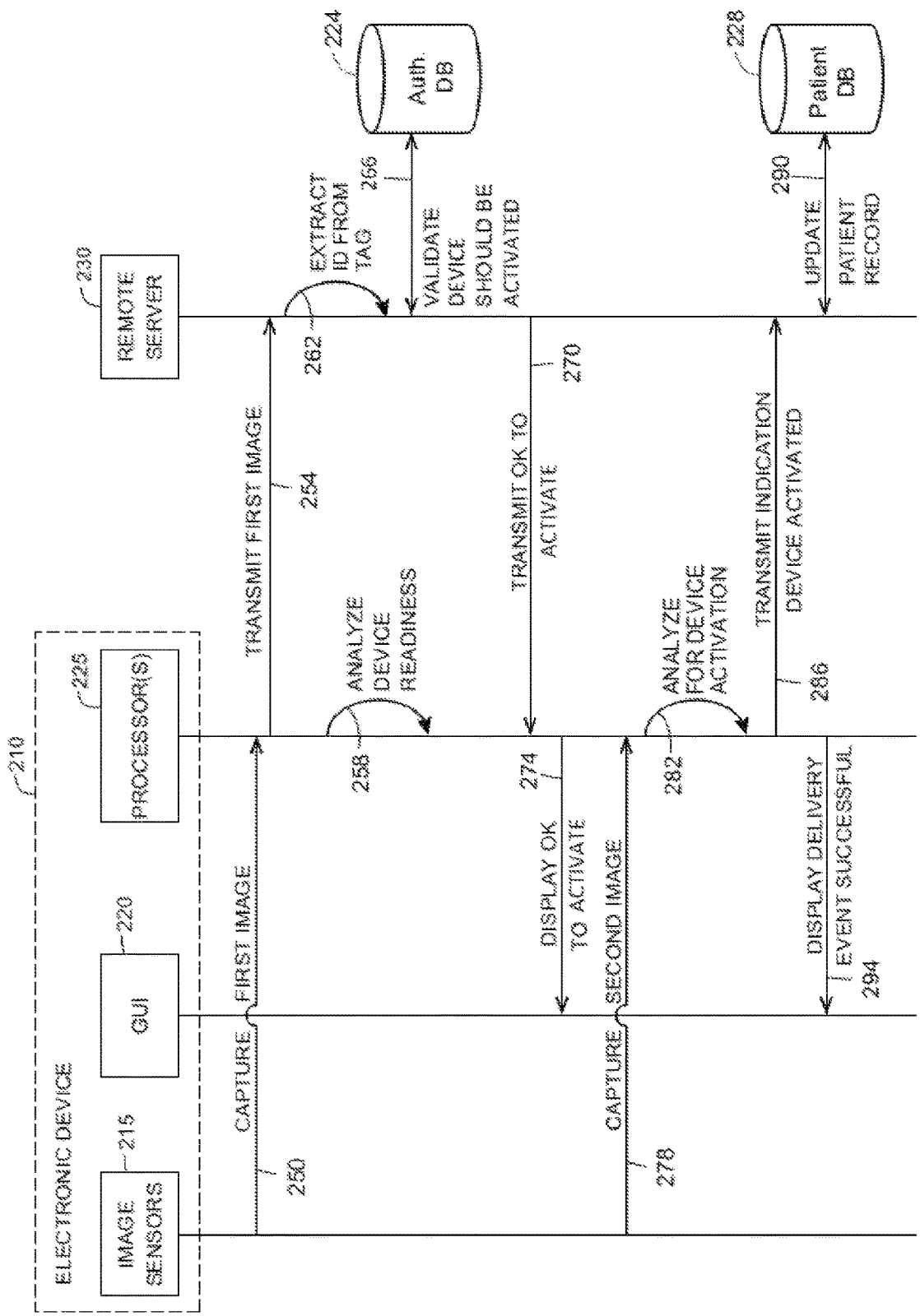
FIG. 2 depicts an example diagram associated with verifying that the medical delivery device contains appropriate medication and updating a patient's medical record.

Referring to FIG. 2, illustrated is a signal diagram 200 associated with verifying the activation of a medical delivery device (such as one of the medical delivery devices 105, 700, or 750) and updating a corresponding patient record. In particular, FIG. 2 includes an electronic device 210 (such as the electronic device 110 as described with respect to FIG. 1) and a remote server 230 (such as the patient monitoring server 130 as described with respect to FIG. 1). The electronic device 210 comprises at least one image sensor 215, a graphical user interface (GUI) 220, and one or more processor(s) 225. In some embodiments, the electronic device 210 may execute instructions contained in an application stored in a memory to implement the steps described in signal diagram 200. The remote server may be communicatively coupled to an authentication database 224 (such as the authentication database 124 as described with respect to FIG. 1) and a patient record database 228 (such as the authentication database 128 as described with respect to FIG. 1). It should be appreciated that the electronic device 210 may be any electronic device associated with the user and/or the patient. Although only one electronic device 210 is depicted in FIG. 2, it should be appreciated that the remote server 230 may be in communication with multiple electronic devices 210 to verify the medication associated with multiple patients and to correspondingly update the respective patient records of the multiple patients.

Figure 7A:
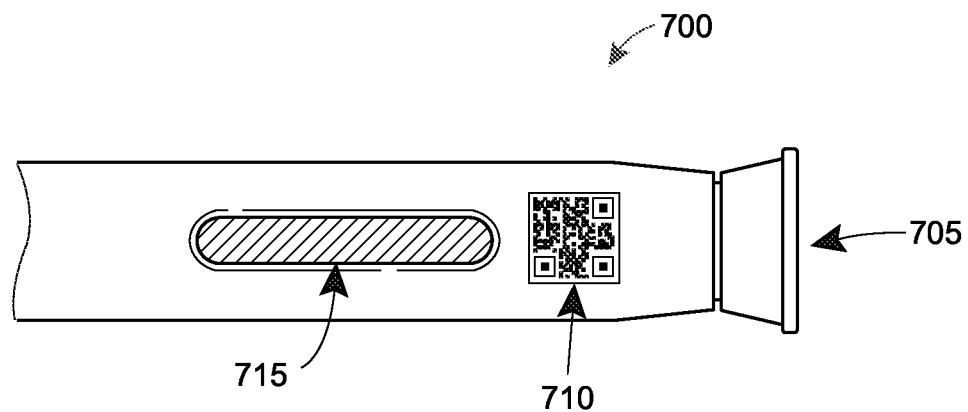
FIG. 7A depicts an example autoinjector prior to activation in accordance with some embodiments.

The signal diagram 200 may begin when the image sensor 215 captures (250) a first image of the medical delivery device. According to embodiments, the first image may include one or more characteristics that the medical delivery device is ready and/or primed to deliver medication, as well as an identification (e.g., a tag) associated with the medical delivery device. With reference to FIG. 7A, an example first image is depicted for embodiments in which the medical delivery device is an autoinjector. The first image may depict both a tag 710 located or disposed on a medical delivery device 700 and a security feature of the medical delivery device that is only present when the medical delivery device is ready or initiated to administer the medication (e.g., needle cap 705 or a protruded button). The first image may also depict a medication chamber 715 as a color indicative of still containing the stored medication. Although FIG. 7A depicts tag 710 as a QR-code, it should be appreciated that other types of tags are envisioned (e.g., 3-D barcode, RFID, NFC, etc.).

Returning to FIG. 2, after the image sensor 215 captures the first image of the medical delivery device, the processor(s) 225 may transmit (254) image data corresponding to the first image to the remote server 230. The processor(s) 225 may use any channel of communication capable of transmitting image data to send the first image data to the remote server 230. The remote server may obtain and/or extract (262) encoded identification information from the first image data, where the extracted information may be representative of the identification of the medical delivery device (e.g., a tag). In some embodiments, the encoded information may include a Uniform Resource Locator (URL) at which the identification information is hosted. Accordingly, extracting the encoded information may including obtaining the information hosted at the indicated URL. The extracted information may include, for example, information describing at least one of the name of the medication, a unique identifier to the particular dosage, and/or a batch and/or lot number indicative of the source of the medication.

Using the extracted identification, the remote server 230 may validate and/or determine (266) that the medical delivery device should be activated. In particular, the remote server 230 may query the authentication database 224 to determine whether the medication contained in the medical delivery device is authentic. In some embodiments, the medication manufacturer may ensure that identification information for every medication is entered into the authentication database 224. In these embodiments, if the authentication database 224 contains a record corresponding to the identification information encoded in the captured tag, it is likely that the medication is authentic. Conversely, if the encoded identification information extracted from the tag is not found in the authentication database 224, it is likely that the medication is counterfeit and the patient should not receive the medication. The authentication server 224 may contain other data useful for determining authenticity. For example, the authentication database 224 may also include shipping information corresponding to where a particular batch of medication was sent. If the query to the authentication server 224 occurred in a region different than a region indicated in the record stored on the authentication server 224, it may be an indication that the medication is counterfeit or stolen.

The authentication server 224 may further store information about the expiration of medication and any recall notices associated with a medication. Accordingly, if the remote server 230 is able to find a record in the authentication database 224 associated with a medical delivery device, the remote server 230 may ensure that the patient is not administered expired medications. For example, if the record for a medication at the authentication database 224 indicates that the medication expires on June 4$^{th}$ of a given year, and the query occurs on July 15$^{th}$ of the same year, then the remote server 230 may transmit an indication that the medication is expired. Similarly, the authentication database 224 may contain a record of medications (or batch and/or lot numbers of a medication) that have been recalled. If the encoded identification information from the tag matches or aligns with a record associated with a recall, then the remote server 230 may transmit an indication that the medication has been recalled.

Once the remote server 230 determines that the medication is likely authentic, not expired, and has not been recalled, the remote server 230 may transmit (270) an indication that the user should activate the medical delivery device. Further, in some embodiments, the indication activate the medical delivery device may include a medication guide in accordance with regulations pertaining to risk evaluation and mitigation strategy (REMS) as established by the Food and Drug Administration (FDA). If the medication is likely counterfeit, expired, or recalled, the remote server 230 may transmit an indication that the user should attempt to use a different medical delivery device. In some embodiments, the indication to use a different medical delivery device may also include instructions to safely dispose of the unusable medical delivery device.

Additionally, the processor(s) 225 may analyze (258) the first image data to ensure the medical delivery device is ready to deliver the medication. The processor(s) 225 may analyze the first image data using image histogram analysis and/or augmented reality techniques to determine the presence of at least one readiness characteristic in the image. This at least one readiness characteristic may indicate that the medical delivery device is primed and/or prepared for administration to the patient. For example, in embodiments where the medical delivery device is an autoinjector, the processor(s) 225 may determine, in the image, the presence of a representation of a needle cap or of the protrusion of a button on the autoinjector by analyzing the shape of the autoinjector and comparing it to at least one predetermined (e.g., known) shape of an autoinjector. In this example, the processor(s) 225 may compare the first image data to stored image data representative of the autoinjector both having and lacking a needle cap. Similarly, the processor(s) 225 may compare the first image data to stored image data representative of the autoinjector having the button both protruded and depressed. In the same embodiments, if the processor(s) 225 determines that the needle cap is on the autoinjector and/or the button is protruded, the autoinjector may be ready to deliver the medication. It should be appreciated that the processor(s) 225 is capable of analyzing the first image data for any number of unique readiness characteristic, whether individually or in combination with one another, that may indicate the readiness of any medical delivery device.

In some embodiments, the processor(s) 225 may analyze the readiness of the medical delivery device concurrently with the remote server 230 validating the appropriateness of the medication. In other embodiments, the readiness of the medical delivery device is determined by the processor(s) 225 prior to the processor 225 transmitting the first image data to the remote server 230. In still other embodiments, the processor(s) 225 may wait until receiving the indication that the user should administer the medication before analyzing the readiness of the medical delivery device.

Once the processor(s) 225 has both analyzed the first image data to determine that the device is ready to be activated and has received the indication from the remote server 230 that the medical delivery device should be activated, the GUI 220 may display (274) an indication that the user should activate the medical delivery device. In some embodiments, the GUI 220 may further display instructions detailing how to properly activate the medical delivery device.

Figure 7B:
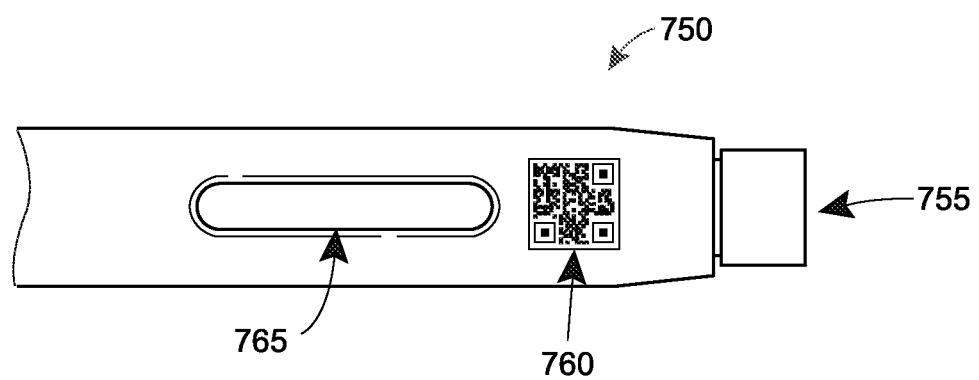
FIG. 7B depicts an example autoinjector after to activation in accordance with some embodiments.

After the user has activated the medical delivery device, the image sensor 215 may capture (278) a second image of the medical delivery device. With reference to FIG. 7B, an example second image is depicted for embodiments in which the medical delivery device is an autoinjector. The second image includes data representative of at least one characteristic that indicates that the medical delivery device 750 has been activated. It should be appreciated that any number of characteristics may indicate the activation of the medical delivery device. For example, the second image may depict an empty medication chamber 765 on the medical delivery device or a safety feature of the medical delivery device that is present after the medical delivery device has been activated (e.g. needle shield 755). Other examples that may be depicted in the second image include a change in color in a portion of the medical delivery device, a change in shape of the medical delivery device, a change in the position of a button (e.g. the button is depressed after activation), and/or a change to existing lettering or images and/or the exposure of previously unseen lettering or images on the outside of the medical delivery device (i.e., the medical delivery device may expose a tag 760 upon activation). The tag 760 used to identify the medical delivery device may also be depicted in the second image. Although FIG. 7B depicts tag 760 as a QR-code, it should be appreciated that other types of tags are envisioned (e.g. 3-D barcode, RFID, NFC, etc.).

Returning again to FIG. 2, the processor(s) 225 may analyze (282) image data of the second image to ensure that the medical delivery device has been activated. The processor(s) 225 may analyze the second image data using similar image histogram analysis and/or augmented reality techniques as performed on the first image data to determine if at least one characteristic indicative that the medical delivery device has been activated is represented in the second image. For example, in some embodiments, a chamber in which the medical delivery device stores the medication changes color once the medication is fully expelled. In these embodiments, if the processor(s) 225 detect an image intensity of a color typically associated with an empty medication chamber is focused in a region and shape associated with the medication chamber of the medical delivery device, the processor(s) 225 may then determine that the medical delivery device has been activated and the medication delivered to the patient. In additional embodiments, at least one security feature associated with a medical delivery device (e.g. a needle shield on an autoinjector) may be detected by analyzing the shape of the medical delivery device in the second image. Detection of such a feature may also be indicative that the medical delivery device has been activated. It should be appreciated that the processor(s) 225 is capable of analyzing the second image for any number of unique characteristics, whether individually or in combination with one another, that may indicate whether the medical delivery device has been activated (or not).

Generally, it may be determined whether the medical delivery device has been activated by analyzing the second image whether the second image indicates that the medical delivery device has been activated. For example, this involves determining whether the second image represents at least the at least one characteristic indicative that the medical delivery device has been activated. In one example, this can be done by comparing the second image to another image (which is received as part of the disclosed method), and determining, based upon the result of that comparison, whether the second image indicates that the medical delivery device has been activated. The other image may be predetermined (e.g. generated before execution of the disclosed method ensues and stored in a database) and retrieved to serve as input for the comparison. Alternatively, the other image may be generated during execution of the disclosed method (for example, as part of the disclosed method). For example, the other image information may be contained in the first image. The at least one characteristic indicative that the medical delivery device has been activated may therefore be determined by comparing the second image to a predetermined image (such as the other image) representing the at least one characteristic indicative that the medical delivery device has been activated. Alternatively or additionally, the at least one characteristic indicative that the medical delivery device has been activated may be determined by comparing the second image to the first image and detecting a difference between the respective representations of the medical delivery device, which difference corresponds to the at least one characteristic indicative that the medical delivery device has been activated. Wherever in this disclosure a comparison of image data or images (for example digital images) is mentioned, such comparison may be effected by for example a pixel-wise comparison or a block-wise similarity analysis between color values of the respective sets of image data or images (for example digital images). Any other suitable algorithm may also be applied to the same effect. In another example, determining whether the second image represents at least the at least one characteristic indicative that the medical delivery device has been activated may be done by analyzing whether the second image contains or lacks a certain image feature (such as a two-dimensional graphical code, e.g. a barcode, a QR code, or a GS1 code), the presence or absence of that image feature being the at least one characteristic indicative that the medical delivery device has been activated. In an even further example, determining whether the second image represents at least the at least one characteristic indicative that the medical delivery device has been activated may be done by analyzing only the second image, for example as to its color distribution (color histogram). The color distribution being within a predetermined limit equal to a predetermined color histogram can be set as a condition for the second image indicating that the medical delivery device has been activated. If such an equality is determined, it is thus determined that the medical delivery device has been activated.

According to embodiments, once the processor(s) 225 determines that the medical delivery device has been activated, the processor(s) 225 may transmit (286) an indication to the remote server 230 that the medical delivery device has been activated. In some embodiments, this indication may include the second image. In these embodiments, the remote server 230 may then analyze the second image to determine that the medical delivery device has been activated.

In response, the remote server 230 may access and update (290) a record in the patient record database 228 associated with the patient. The record may be updated to include details about the medication delivery event that the processor(s) 225 determined and/or confirmed to have occurred. These details may include information that is helpful for an HCP in monitoring a patient's compliance with a medication regimen. For example, the time and date of the delivery, the location of the delivery, the name of the medication, the batch and/or lot number of the medication, the name of the user who administered the medication, and/or the like may be recorded in a patient record contained in the patient record database 228. In some embodiments, the remote server 230 may send a confirmation to the electronic device 210 indicating that the patient record was updated.

The patient record database 228 may also be useful for pharmacovigilance. For example, when a recall for a medication occurs, an HCP or other party may query the patient record database to determine which patients have received the recalled medication. The HCP or other party may proactively contact the patient and provide the patient with instructions to mitigate the risk of harm that may have been caused by receiving the recalled medication. Further, it may allow regulatory agencies and/or manufacturers to better track and trace medications in the event the patient experiences an adverse reaction and/or other medical condition. As an example, if a patient experiences an adverse reaction in the course of a medication regimen, a patient record associated with the patient may be analyzed to determine the potential cause of the adverse event. This information can be analyzed to improve and adjust the medication regimens of patients that take the same or similar medications (as determined by querying the patient record database 228) to prevent further adverse reactions from occurring.

Additionally, the GUI 220 may also display (294) an indication that the delivery event was successful. In embodiments in which the remote server 230 sends a confirmation, an indication that the delivery event was recorded in the patient record database 228 may also be displayed by the GUI 220.

Example Reminder Functionality

Some embodiments may also include a routine or application executed by the electronic device that reminds a user and/or a patient when to administer medication via a medical delivery device. For simplicity's sake, the below description refers to the routine running on an electronic device of the user. It is also envisioned that the routine can run on an electronic device associated with the patient or at a remote server. In embodiments, the electronic device may store in a memory a medication regimen associated with the patient. In some embodiments, the memory is synchronized with data stored in a patient record database at an HCP. In other embodiments, the memory is manually populated through user interaction with a GUI on the electronic device.

The medication regimen contains a record of medications that are to be administered to a patient as well as when the medications are to be administered. For example, the medication regimen may indicate that a patient is required to receive a first medication for diabetes every other day and to receive a second medication to control allergic reactions to pollen once a week. The medication regimen may also include indications about when to alert a user before a medication should be delivered and, if a medication is missed, when to alert a health care provider. Returning to the previous example, the diabetes medication scheduled to be administered every other day may require closer monitoring and, as such, may alert the user fifteen minutes prior to when a medication is to be delivered and may alert a health care provider if no medication delivery occurs within a day of the scheduled delivery time. Conversely, the allergy medication may require less oversight and alert the user a day prior to an injection and may not alert a health care provider until four days have passed since the scheduled delivery time.

Figure 3:
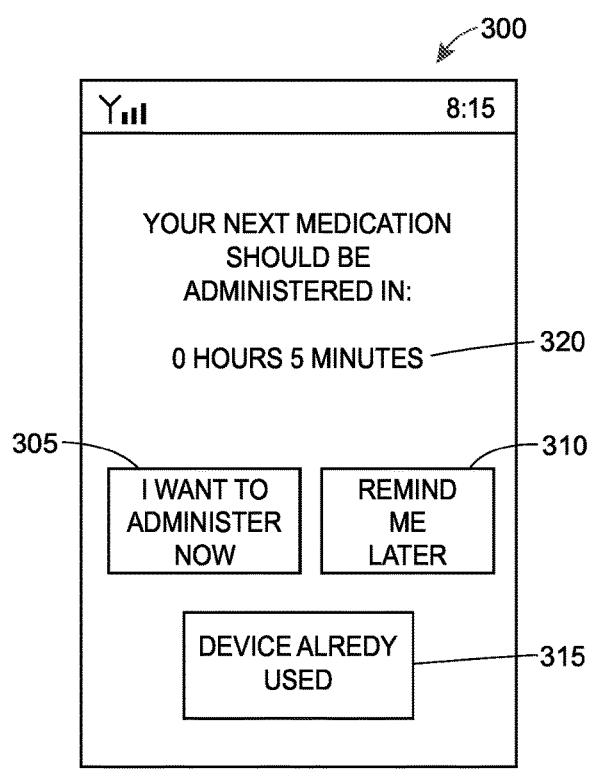
FIG. 3 depicts an example graphical user interface (GUI) of an electronic device associated with a patient receiving a reminder to administer a medication.

The electronic device may alert the user prior to a scheduled delivery time in accordance with the medication regimen. With reference to FIG. 3, an example GUI 300 displaying the alert is depicted. The GUI 300 may include an indication 320 of how much time until a scheduled delivery event is due. Although it is not depicted, the GUI 300 may also indicate the name of the medication that is scheduled to be administered to the patient. The GUI 300 may also provide the user with several options to respond to the alert. For example, a soft key 305 may be provided to receive an indication that the user currently wants to administer the medication to the patient. In some embodiments, in response to the user selecting the soft key 305, the electronic device may present an interface to capture an image of the medical delivery device.

In some instances, the user may not be able to administer the medication to the patient when the GUI 300 displays the reminder alert. As such, the GUI 300 may provide a soft key 310 that enables the user to be reminded at a later time. In some embodiments, in response to the user selecting the soft key 310, the electronic device may present an interface to enable the user to schedule a follow-up reminder. The timing of the follow-up reminder may be a number of hours and/or minutes from the current time, or a specific time in the future. According to embodiments, the reminder routine may not allow the user to schedule a follow-up reminder beyond a certain point in the future (e.g. the reminder routine may disallow follow-up reminders beyond the point in which an HCP is alerted).

In other instances, the user may have already administered the medication to the patient ahead of the schedule indicated in the medication regimen. The GUI 300 may provide a soft key 315 to enable the user to indicate that the medication has already been delivered to the patient. In response to the user selecting the soft key 315, the electronic device may provide an interface that allows the user to manually enter details of the delivery event that already occurred. For example, the interface may prompt the user for at least the time and date of the delivery event, as well as, if possible, an image of the medical delivery device used during the earlier delivery event.

Figure 4:
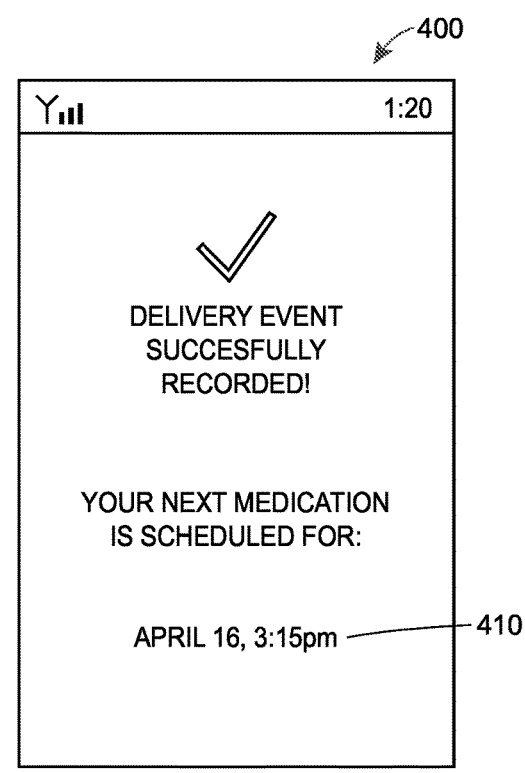
FIG. 4 depicts a GUI of an electronic device associated with a patient receiving confirmation that the medical delivery device was activated.

In some embodiments, after the electronic device has confirmed and/or determined that the medical delivery device was activated and that the medication was delivered to the patient, the electronic device may display an indication that the delivery event was recorded successfully. With reference to FIG. 4, this indication may be provided by a GUI 400. In some embodiments, the GUI 400 may provide a symbol normally associated with a successful event, such as a green check mark. The electronic device may also query the medication regimen to determine when the next scheduled delivery is due. In some embodiments, the GUI 400 may display an indication 410 corresponding to when this next delivery event is scheduled.

Despite the electronic device reminding the user, a patient may still fail to receive a medication according to the medication regimen. If no delivery event is recorded and the time period before an HCP is alerted for a given medication has been reached, the electronic device may generate an alert to an HCP associated with the patient. The alert may inform the HCP that the patient has failed to receive a medication as scheduled and that the HCP should attempt to contact the patient. The alert may be an SMS message to the patient's primary physician and/or caretaker, a status change in a database associated with the HCP (such as the patient record database 128 as discussed with respect to FIG. 1), and/or any other suitable means of informing an HCP that a patient has failed to receive a scheduled medication.

Example Method of User Interaction with the Electronic Device

Figure 5:
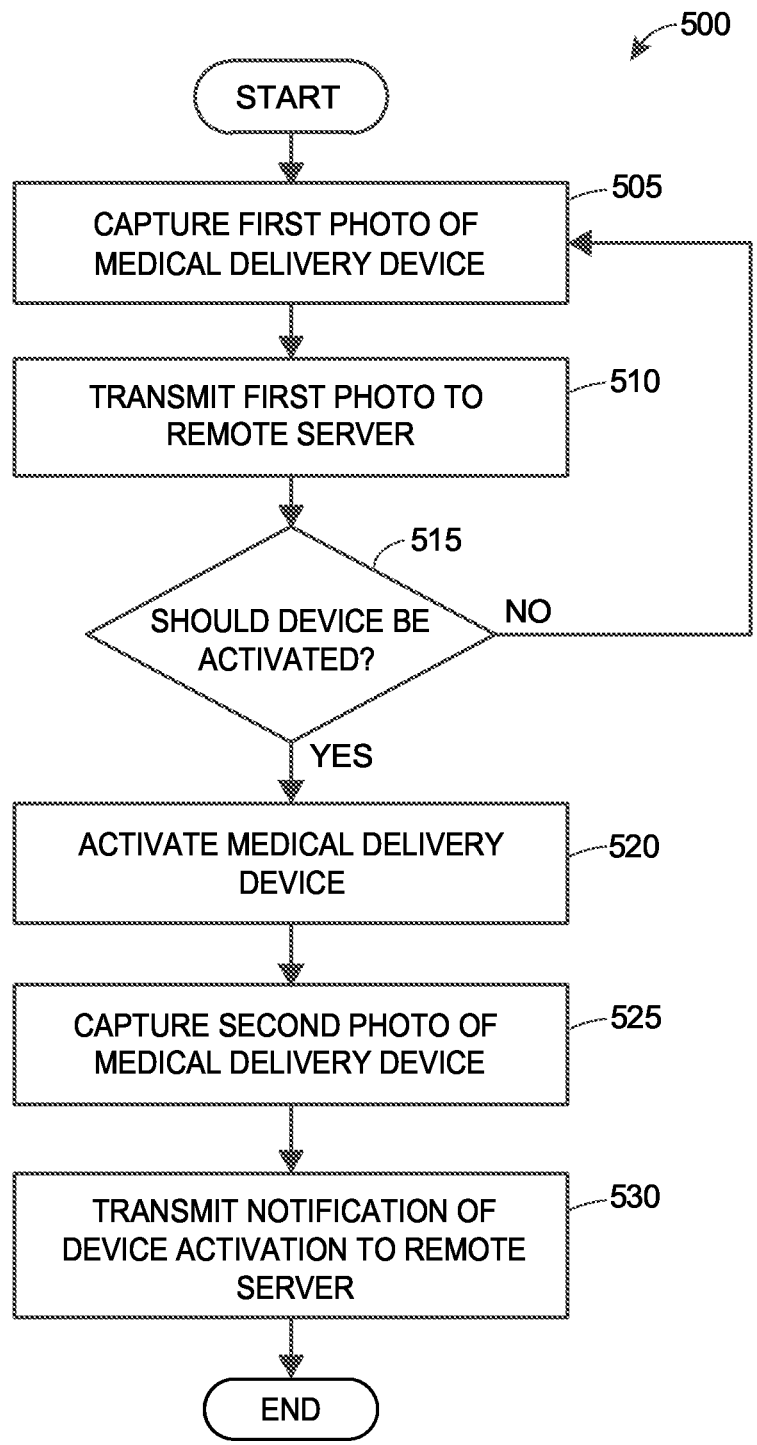
FIG. 5 is a flow diagram associated with a user of an electrical device verifying that the medical delivery device contains appropriate medication and updating a patient's medical record.

Referring to FIG. 5, depicted is a block diagram of an example method 500 for one or more electronic devices to validate the activation of a medical delivery device and to update a patient record associated with the patient. For example, the one or more electronic devices may be an electronic device of a user. The electronic device may be a smartphone or any other type of electronic device (such as the electronic device 110 with respect to FIG. 1) in accordance with method 500.

The method 500 may begin with the electronic device capturing an image of the medical delivery device prior to activating the medical delivery device (block 505). The electronic device may display the captured image on a GUI to enable the user to evaluate the captured image. If the user is not satisfied with the first photo (e.g. the image is too dark or the identification tag associated with the medical delivery device is out of focus), the electronic device may be present an option to capture another image. Once the user is satisfied with the captured image, the electronic device can transmit the image to a remote server that may analyze whether the user should administer the medication (block 510).

After the remote server analyzes the transmitted image, the electronic device may display an indication of whether the user should proceed to activate the medical delivery device (block 515). If the remote server determined that the medical delivery device should not be activated ("NO"), then the electronic device displays an indication that the user should provide an image of a different medical delivery device for analysis (returning to block 505). If the remote server determined that the user should activate the medical delivery device ("YES"), then the electronic device may display an indication that the user should administer the medication to the patient. In response to viewing this indication, the user may activate the medical delivery device (block 520).

In response to the electronic device detecting activation of the medical delivery device, the electronic device can provide an interface to capture a second image of the medical delivery device after it has been activated by the user. The electronic device may then capture the second image of the medical delivery device (block 225). Afterwards, the electronic device may analyze the second image to determine that the medical delivery device has been activated. If the electronic device determines that a delivery has occurred, the electronic device may display a user interface to enable the user to transmit details of the activation event to the remote server. Subsequently, the electronic device may transmit these details to the remote server (block 530). It should be appreciated that in some embodiments, the actions associated with any particular block may occur automatically by the electronic device and without input from the user.

Example Hardware for Electronic Device and Remote Server

Figure 6A:
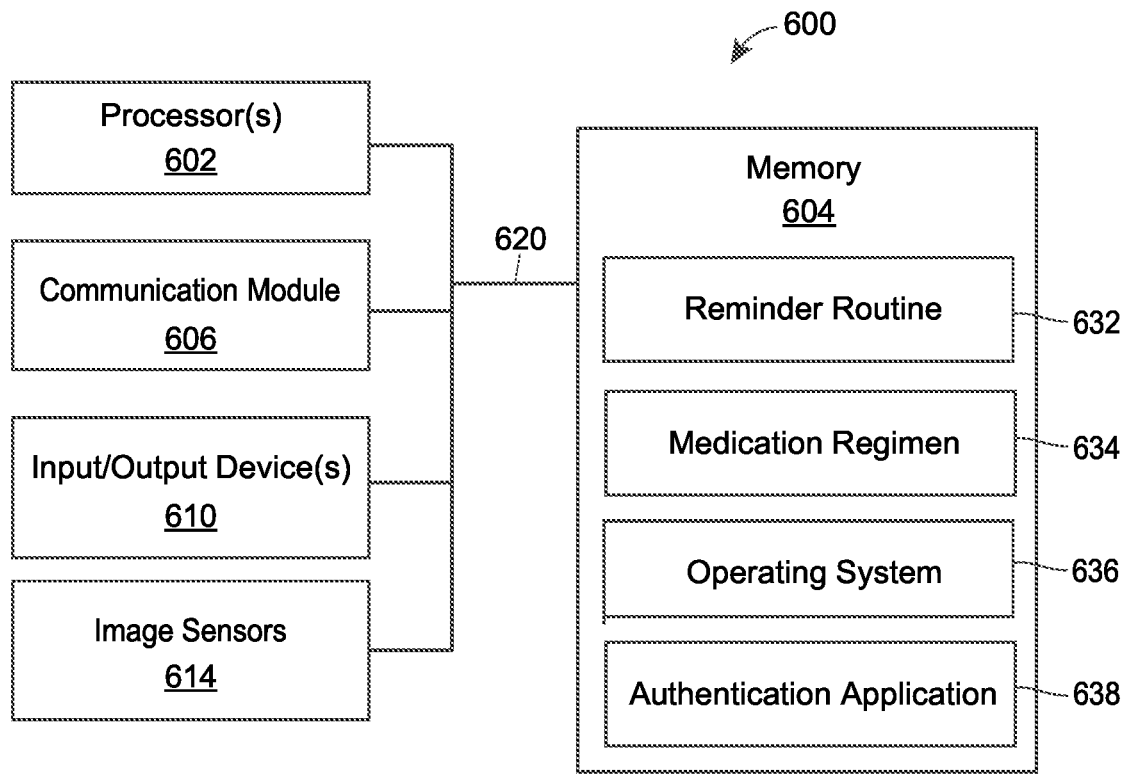
FIG. 6A is a block diagram of an example electronic device used to verify that the medical delivery device contains appropriate medication and update a patient's medical record.

Now referring to FIG. 6A, depicted is an electronic device 600 (such as electronic device 110 with respect to FIG. 1) that may facilitate various of the functionalities discussed herein. The electronic device 600 may include one or more processor(s) 602, as well as a memory 604. The processor(s) 602 can interface with the memory 604 to execute the operating system 636, the authentication application 638, and the reminder routine 632. The reminder routine 632 may access the medication regimen 634 in order to determine when a medication should be administered to a patient. Although depicted as two separate modules, in some embodiments, the reminder routine 632 may be contained within the authentication application 638. The operating system may contain a set of instructions that, when interpreted by the processor(s) 602, cause the electronic device 600 to perform specific functions and routines as described above. The operating system 636 may interface with the reminder routine 632 and the authentication application 638 to determine which instructions should be interpreted by the processor(s) 602. The memory 604 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and/or the like.

The electronic device 600 may further include a communication module 606 configured to communicate data over a communication network. According to some embodiments, the communication module 606 may include a plurality of transceivers that function in accordance with IEEE, 3GPP or other standards (e.g. LTE, CDMA, EVDO, Wi-Fi, and the like). For example, the communication module 606 may transmit images of a medical delivery device via a communication network. The communication module 606 may also receive an indication from a remote server that a user should activate a medical delivery device to administer a medication to a patient. The electronic device 600 may further include one or more image sensors 614 configured to capture image data associated with a medical device. According to embodiments, the image sensors 614 may be CCD or CMOS image sensors, or other types of image sensors. In some embodiments, an image sensor 614 may comprise a plurality of individual photoreceptors.

Additionally, the electronic device 600 may also include at least one input/output device 610 such as, for example, a display screen, a touch sensitive display panel, a soft key, a button, a light, a camera, and others. According to embodiments, the user may interact with the electronic device 600 via the at least one input/output device 610 to capture, via the one or more image sensors 614, an image of a medical delivery device and transmit, via the communication module 606, the image to a remote server. The components 602-614 can be interconnected via a digital bus 620.

Figure 6B:
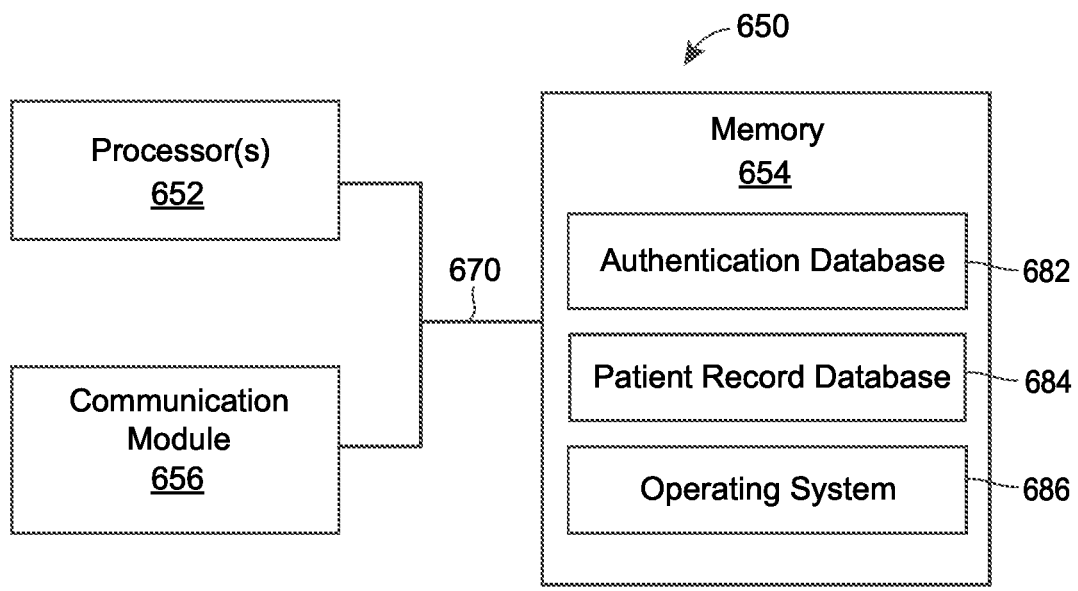
FIG. 6B is a block diagram of an example patient monitoring server used to verify that the medical delivery device contains authentic medication and update a patient's medical record.

With reference to FIG. 6B, depicted is a remote server 650 (such as patient monitoring server 130 with respect to FIG. 1) that may facilitate various of the functionalities discussed herein. The remote server 650 may include one or more processor(s) 652, as well as a memory 654. The remote server 650 may further include a communication module 656 to communicate with an electronic device. In some embodiments, the remote server 650 may perform the functionalities as discussed herein as part of a "cloud" network or can otherwise communicate with other hardware or software components within the cloud to send, retrieve, or otherwise analyze data.

The memory 654 may store the operating system 686, an authentication database 682, and a patient record database 684. The authentication database 682 and the patient record database 684 may be implemented as the authentication database 124 and patient record database 128, respectively, as described with respect to FIG. 1. The operating system may contain a set of instructions that, when interpreted by the processor(s) 652, can cause the remote server 650 to perform the specific functions and routines as described above. The digital bus 670 may interconnect the processor(s) 652, communication module 656, and memory 654.

Referring generally to FIGS. 6A and 6B, it should be appreciated that the electronic device 600 and remote server 650 may include additional or fewer components than depicted. In some implementations, two or more components may be combined and implemented as a single component. In other implementations, a depiction of a single component may represent multiple interconnected components.

It should be understood that, unless a term is expressly defined in this patent using the sentence "As used herein, the term '_' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this disclosure is referred to in this disclosure in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

What is claimed:

1. A system for determining that a medical delivery device capable of administering a medication to a patient has been activated, the system comprising at least an electronic device, the electronic device comprising:
   an image sensor configured to capture images; and
   a user interface configured to display content,
   the system further comprising:
   one or more processors adapted to interface with the image sensor and the user interface, wherein the one or more processors are configured to:
      receive a first set of image data from the image sensor,
      analyze the first set of image data to determine that a medical delivery device is ready to deliver the medication to the patient, wherein the medical delivery device is one of an autoinjector, an on-body injector, an inhaler, a drip chamber, an eye dropper, a nasal spray, or a nebulizer,
      receive a second set of image data from the image sensor,
      analyze the second set of image data to detect a characteristic of the medical delivery device indicative that the medical delivery device has been activated, wherein the characteristic of the medical delivery device is at least one of a characteristic of a needle shield, a characteristic of a chamber that stores the medication, a shape of the medical delivery device, a characteristic of an activation button, a characteristic of a safety feature, or a component that becomes exposed upon activation of the medical delivery device,
      cause the user interface to indicate that the medical delivery device has been activated, and
      cause a remote server to update a medical record corresponding to the patient.

2. The system in claim 1, wherein the first set of image data contains image data representative of at least one of a 2-D barcode or a readiness characteristic, wherein the readiness characteristic comprises at least one of a needle cap and a protruded button.

3. The system in claim 2, wherein to determine that the medical delivery device is ready to deliver a medication to a patient, the one or more processors are configured to verify that the first set of image data contains image data representative of the readiness characteristic.

4. The system in claim 1, further comprising:
a memory to store a medication regimen of the patient, wherein the medication regimen contains a schedule of when a user is to administer the medication to the patient.

5. The system in claim 4, wherein the one or more processors are further configured to:
cause the user interface to display a reminder of when the medication regimen indicates that the user is to administer the medication, and
after confirming that the medical delivery device has administered the medication, cause the user interface to display when a next medication in the medication regimen is to be administered.

6. The system in claim 4, wherein the one or more processors are further configured to transmit, via a communication network, an alert to a health care provider associated with the patient when no medication has been delivered as scheduled in the medication regimen.

7. The system in claim 2, wherein the one or more processors are further configured to:
transmit, to a remote server via a communication network, the first set of image data; and
receive, from the remote server via the communication network, a notification to activate the medical delivery device.

8. The system in claim 7, wherein transmitting the first set of image data causes the remote server to:
receive, via the communication network, the first set of image data from the electronic device;
obtain, from the first set of image data, an identifier associated with the medical delivery device;
compare the identifier to a record contained in an authentication database;
determine that the medication should be delivered to the patient; and
transmit, to the electronic device, a notification to activate the medical delivery device.

9. The system in claim 7 wherein receiving, the notification to activate the medical delivery comprises:
receiving, via the communication network, a notification that the remote server determined the medication is not counterfeit, the medication is not expired, and the medication has not been recalled.

10. The system in claim 2, wherein the one or more processors are further configured to:
transmit, to the remote server via the communication network, an indication that the medical delivery device was activated.

11. The system in claim 10, wherein transmitting the indication that the medical delivery device was activated causes the remote server to:
update a medical record in a patient record database with information about a delivery event, wherein the information comprises at least one of a time and date of the delivery, a location of the delivery event, a name of the medication, a batch number, a lot number, or a name of the user who administered the medication.

12. A method for enabling a user to detect the activation of a medical delivery device capable of administering a medication to a patient with an application executing on a web-enabled mobile device, where the web-enabled mobile device includes one or more processors, a memory coupled to the one or more processors, and an image sensor configured to capture images of the medical delivery device, wherein the medical delivery device is one of an autoinjector, an on-body injector, an inhaler, a drip chamber, an eye dropper, a nasal spray, or a nebulizer, the method comprising:
the application causing the image sensor to capture a first image of the medical delivery device;
analyzing, by the one or more processors, the first image to determine that the medical delivery device is ready to deliver the medication to the patient;
the application causing the image sensor to capture a second image of the medical delivery device;
analyzing, by the one or more processors, the second image to detect a characteristic of the medical delivery device indicative that the medical delivery device was activated, wherein the characteristic of the medical delivery device is at least one of a characteristic of a needle shield, a characteristic of a chamber that stores the medication, a shape of the medical delivery device, a characteristic of an activation button, a characteristic of a safety feature, or a component that becomes exposed upon activation of the medical delivery device;
indicating, via the user interface in the application, that the medical delivery device was activated; and
the application causing a remote server to update a medical record corresponding to the patient.

13. The method of claim 12, wherein analyzing the first image comprises:
identifying, from the first image, at least one of a QR code and a readiness characteristic, wherein the readiness characteristic comprises at least one of a needle cap or a protruded button.

14. The method of claim 12, further comprising:
displaying, via the user interface in the application, an indication of when a medication regimen indicates that the user is to deliver the medication; and
after determining that the medical delivery device has delivered the medication, displaying, via the user interface in the application, when a next medication in the medication regimen is to be delivered.

15. The method of claim 14, further comprising:
the application alerting, via a communications network, a health care provider associated with the patient when no medication has been delivered as scheduled in the medication regimen.

16. The method of claim 12, further comprising:
transmitting from the web-based mobile device, to a remote server via a communication network, the first image; and
receiving at the web-based mobile device, via the communication network, a notification to activate the medical delivery device.

17. The method of claim 16, wherein transmitting the first image causes the remote server to:
receive, via the communication network, the first image from the web-enabled mobile device;
read, from the first image by one or more processors at the remote server, an identifier associated with the medical delivery device;
compare, by the one or more processors at the remote server, the identifier to a record contained in an authentication database to determine that the medication should be delivered to the patient; and transmit, via the communication network, a notification to activate the medical delivery device to the web-enabled mobile device.

18. The method of claim 17, wherein transmitting the first image further causes the remote server to:

analyze the authentication database to determine that the medication is not counterfeit, the medication is not expired, and the medication has not been recalled.

19. A computer-implemented method for determining that a medical delivery device capable of administering a medication to a patient has been activated, wherein the medical delivery device is one of an autoinjector, an on-body injector, an inhaler, a drip chamber, an eye dropper, a nasal spray, or a nebulizer, the method comprising:

receiving, via a communication network, a first image, wherein the first image depicts the medical delivery device;

analyzing, by one or more processors, the first image to obtain an identification of the medical delivery device;

using the identification, determining, by the one or more processors, that the medication within the medical delivery device should be administered to the patient;

transmitting, via the communication network, a first indication that a user should administer the medication;

receiving, via the communication network, a second indication that the medical delivery device has been activated, wherein the second indication includes a second image depicting the medical delivery device;

analyzing, by the one or more processors, the second image to detect a characteristic of the medical delivery device indicative that the medical delivery device has administered the medication, wherein the characteristic of the medical delivery device is at least one of a characteristic of a needle shield, a characteristic of a chamber that stores the medication, a shape of the medical delivery device, a characteristic of an activation button, a characteristic of a safety feature, or a component that becomes exposed upon activation of the medical delivery device; and based on the second indication, updating, by the one or more process, a medical record corresponding to the patient.

20. The computer-implemented method of claim 19, wherein analyzing the first image further comprises:

analyzing, by the one or more processors, the first image to detect a barcode depicted in the first image;

determining, by the one or more processors, a Universal Resource Locator (URL) indicated by the barcode; and obtaining, by the one or more processors, the identification from information hosted at the indicated URL.

21. The computer-implemented method of claim 19, wherein analyzing the first image further comprises:

analyzing, by the one or more processors, extracted data corresponding to the first image, wherein the extracted data was extracted via a Near-Field Communication (NFC) sensor.

22. The computer-implemented method of claim 19, wherein determining that the medication should be administered further comprises:

using the identifier, querying, by the one or more processors, an authentication database that stores information relating to the medication; and determining, by the one or more processors, that the authentication database indicates that the medication is not counterfeit, expired, or recalled.

23. A non-transitory computer-readable storage medium having a memory and computer-executable instructions stored in the memory, said instructions, when executed by one or more processors of one or more computers, cause the one or more computers to execute a computer-implemented method for determining that a medical delivery device capable of administering a medication to a patient has been activated, wherein the medical delivery device is one of an autoinjector, an on-body injector, an inhaler, a drip chamber, an eye dropper, a nasal spray, or a nebulizer, the method comprising:

receiving, via a communication network, a first image, wherein the first image depicts the medical delivery device;

analyzing, by the one or more processors, the first image to obtain an identification of the medical delivery device;

using the identification, determining, by the one or more processors, that the medication within the medical delivery device should be administered to the patient;

transmitting, via the communication network, a first indication that a user should administer the medication;

receiving, via the communication network, a second indication that the medical delivery device has been activated; wherein the second indication includes a second image depicting the medical delivery device;

analyzing, by the one or more processors, the second image to detect a characteristic of the medical delivery device indicative that the medical delivery device has administered the medication, wherein the characteristic of the medical delivery device is at least one of a characteristic of a needle shield, a characteristic of a chamber that stores the medication, a shape of the medical delivery device, a characteristic of an activation button, a characteristic of a safety feature, or a component that becomes exposed upon activation of the medical delivery device; and based on the second indication, updating, by the one or more processors, a medical record corresponding to the patient.

24. At least one computer having at least one processor, the at least one computer being operatively coupled to the non-transitory computer-readable storage medium of claim 23, for executing, by the at least one processor, the instructions stored in the memory of the non-transitory computer-readable storage medium.

* * * * *